(12) United States Patent
Frank et al.

(10) Patent No.: US 7,560,489 B2
(45) Date of Patent: Jul. 14, 2009

(54) STABILIZED PROSTAGLANDIN E COMPOSITION

(75) Inventors: Daniel W. Frank, Broomall, PA (US); Yiping Wang, Howell, NJ (US)

(73) Assignee: NexMed Holdings, Inc., East Windsor, NJ (US)

( * ) Notice: Subject to any disclaimer, the term of this patent is extended or adjusted under 35 U.S.C. 154(b) by 310 days.

(21) Appl. No.: 11/546,196

(22) Filed: Oct. 11, 2006

(65) Prior Publication Data

US 2008/0090911 A1 Apr. 17, 2008

(51) Int. Cl.
*A61K 31/557* (2006.01)
(52) U.S. Cl. ..................................................... 514/573
(58) Field of Classification Search .................... 514/573
See application file for complete search history.

(56) References Cited

U.S. PATENT DOCUMENTS

| | | | | |
|---|---|---|---|---|
| 4,036,954 A | * | 7/1977 | Murakami et al. | 514/573 |
| 4,113,882 A | * | 9/1978 | Okazaki et al. | 514/573 |
| 4,483,846 A | * | 11/1984 | Koide et al. | 424/433 |
| 4,552,751 A | * | 11/1985 | Inaba et al. | 424/449 |
| 4,806,354 A | * | 2/1989 | Green | 424/687 |
| 5,525,348 A | * | 6/1996 | Whitbourne et al. | 424/423 |
| 5,739,113 A | * | 4/1998 | Lee | 514/21 |
| 2004/0044328 A1 | * | 3/2004 | Kemp et al. | 604/500 |
| 2004/0131664 A1 | * | 7/2004 | Mo et al. | 424/449 |
| 2004/0185100 A1 | * | 9/2004 | Franz | 424/472 |
| 2005/0181030 A1 | * | 8/2005 | Mo et al. | 424/448 |
| 2006/0051391 A1 | * | 3/2006 | Dvoskin et al. | 424/422 |
| 2008/0090911 A1 | * | 4/2008 | Frank et al. | 514/573 |

* cited by examiner

*Primary Examiner*—Raymond J Henley, III
(74) *Attorney, Agent, or Firm*—Olson & Cepuritis, Ltd.

(57) ABSTRACT

A prostaglandin E composition comprises are substantially free from $C_1$-$C_4$ alcohols and include the prostaglandin E compound together with a ($C_1$-$C_4$)-alkyl($C_8$-$C_{22}$)carboxylic ester (e.g., ethyl laurate), an N,N-di($C_1$-$C_8$)alkylamino substituted, ($C_4$-$C_{18}$)alkyl($C_2$-$C_{18}$)carboxylic ester and/or a pharmaceutically acceptable addition salt thereof, and optionally, a viscosity enhancing agent such as guar gum. The prostaglandin E composition can be combined with an aqueous alcoholic diluent to form a pharmaceutical composition for topical application to a patient, for example, to treat sexual dysfunction. The prostaglandin E compositions are stable for prolonged periods of storage at room temperature.

27 Claims, No Drawings

STABILIZED PROSTAGLANDIN E COMPOSITION

TECHNICAL FIELD

This application relates to room temperature stable, non-aqueous prostaglandin E compound-containing compositions.

BACKGROUND OF THE INVENTION

Prostaglandins may exhibit vasodilation or vasoconstriction, smooth muscle stimulation or depression. Prostaglandins of the E group, such as Prostaglandin $E_1$ ($PGE_1$), have been reported as having utility for the treatment of sexual erectile dysfunction when injected intracavemously as an aqueous solution in physiological saline, Mahmond et al., *J. Urology* 147:623-626 (1992), or applied topically. However, the prostaglandins, such as $PGE_1$, are relatively insoluble in water, and are also relatively unstable. As a result, prostaglandin solutions for injection are prepared shortly prior to use, and are a relatively inconvenient expedient.

Attempts to stabilize $PGE_1$ in aqueous systems by the use of α-cyclodextrin or β-cyclodextrin complexes have been reported. Wiese et al., *J. Pharm. Sciences* 80:153-156 (1991); Szejtli, J., "Industrial Applications of Cyclodextrins," *Inclusion Compounds III*, Academic Press, London, England (1984), pp. 355-368. However, even the aqueous $PGE_1$ preparations so-stabilized have a relatively short shelf life that limits their practical utilization.

It has now been found that the stability of prostaglandins of the E group can be substantially enhanced without sacrificing bioavailability by including a prostaglandin E compound in a composition containing a ($C_1$-$C_4$)-alkyl($C_8$-$C_{22}$)carboxylic ester, but substantially free from $C_1$-$C_4$ alcohols.

SUMMARY OF THE INVENTION

Prostaglandin E (PGE) group compounds are stabilized as non-aqueous compositions that are substantially free from $C_1$-$C_4$ alcohols and include the prostaglandin E compound together with a ($C_1$-$C_4$)-alkyl($C_8$-$C_{22}$)carboxylic ester (e.g., ethyl laurate). Preferably, an N,N-di($C_1$-$C_8$)alkylamino substituted, ($C_4$-$C_{18}$)alkyl($C_2$-$C_{18}$)carboxylic ester and/or a pharmaceutically acceptable addition salt thereof, and optionally, a viscosity enhancing agent such as a polysaccharide, a modified polysaccharide, a cellulose derivative, a cross-linked polyacrylic acid, or a salt thereof, can also be present in the composition.

In one embodiment, the composition is included in a packaged, multi-component dosage form, which comprises a sealed actives compartment containing a prostaglandin E group composition of the invention, and a sealed diluent compartment containing a pharmaceutically compatible diluent for forming a prostaglandin E topical dosage form ready for administration. The diluent is combinable with the prostaglandin E group composition to provide a pharmaceutical composition for topical application to a patient. The diluent can contain a $C_1$-$C_4$ alcohol (e.g., ethanol), water, and one or more buffering agents to provide a physiologically acceptable pH for the topical dosage form when the diluent is combined with the prostaglandin E composition prior to use. The topical dosage form, which results from combination of the diluent and the prostaglandin E composition preferably is in the form of a cream, a gel, or an ointment.

A preferred N,N-di($C_1$-$C_8$)alkylamino substituted, ($C_4$-$C_{18}$)alkyl ($C_2$-$C_{18}$)carboxylic ester is dodecyl 2-(N,N-dimethylamino)-propionate, a pharmaceutically acceptable addition salt thereof, or a combination thereof.

In one preferred embodiment, the prostaglandin E composition is substantially free from $C_1$-$C_4$ alcohols and comprises about 0.025 to 10 percent by weight of a prostaglandin E group compound, about 0.025 to 40 percent by weight of a N,N-di($C_1$-$C_8$)alkylamino substituted, ($C_4$-$C_{18}$)alkyl($C_2$-$C_{18}$)carboxylic ester skin permeation enhancer, such as dodecyl 2-(N,N-dimethylamino)-propionate or a salt thereof, about 0.25 to about 40 percent by weight of a ($C_1$-$C_4$)-alkyl ($C_8$-$C_{22}$)carboxylic ester (preferably ethyl laurate). Optionally, the composition can include about 0.05 to 40 percent by weight of a viscosity enhancing agent (e.g., guar gum).

A particularly preferred multi-part dosage form embodiment comprises a sealed actives compartment containing a PGE composition of the invention, and a sealed diluent compartment containing a diluent for admixture with the PGE composition to provide a topical dosage form. The diluent comprises about 5 to 95 parts by weight of a $C_1$-$C_4$ alcohol (preferably ethanol), and about 5 to 95 parts by weight water, preferably an amount of one or more buffering agents sufficient to maintain a physiologically acceptable pH in a topical PGE dosage form, and optionally, about 0.001 to 5 parts by weight of an antifoam agent, in a sealed compartment of container. The sealed diluent compartment is packaged together with the sealed actives compartment, preferably in the form of a two-compartment pouch or packet, in which the two compartments are separated by a frangible seal. In some embodiments, instructional indicia, such as a label, pamphlet, booklet, brochure, video tape, CD-ROM, and the like can be included with the dosage form so as to inform the user about the contents, how to combine the diluent and prostaglandin E composition into a topical dosage form, how to apply the dosage form, and the like. The topical dosage form prepared by combining the diluent and prostaglandin E composition is viscous and substantially non-flowing, such as a cream, gel, or ointment.

Topical dosage forms prepared from the stabilized PGE compositions of the invention are useful for amelioration of sexual dysfunction in human patients, e.g., male impotence, premature ejaculation, female sexual arousal disorder, and the like.

DESCRIPTION OF PREFERRED EMBODIMENTS

Prostaglandin E (PGE) is a known compound that can be represented by the formula

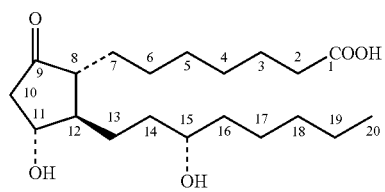

Compounds derived from the foregoing structure and having the 9-oxo, 11α-hydroxy substituents as well as unsaturation in the side chains are known as compounds of the prostaglandin E group, hereinafter collectively referred to as PGE compounds. The compounds of this group include prostaglandin $E_1$ ($PGE_1$) represented by the formula

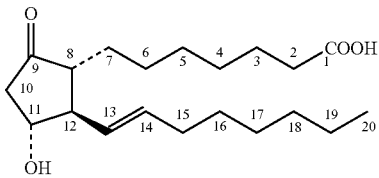

prostaglandin $E_2$ (or $PGE_2$) represented by the formula

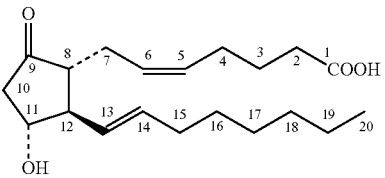

prostaglandin $E_3$ (or $PGE_3$) represented by the formula

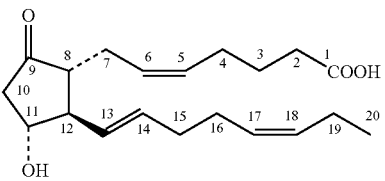

as well as the pharmaceutically acceptable salts thereof.

PGE compounds have useful therapeutic activity as vasodilators and have been utilized to treat male and female sexual disorders, to control lipid metabolism, to treat ulcers, to treat inflammatory skin lesions, and the like therapeutic applications.

PGE compounds are relatively unstable, however, and tend to decompose, especially in aqueous solutions or in an aqueous environment. It has now been found however, that these compounds can be effectively stabilized in non-aqueous media that are substantially free from $C_1$-$C_4$ alcohols and include a $(C_1$-$C_4)$-alkyl$(C_8$-$C_{22})$carboxylic ester, such as ethyl laurate. The PGE compositions of the invention can be combined with a suitable diluent (e.g., a buffered aqueous alcohol combination) to form a topical dosage form, such as a cream, gel, ointment, and the like, prior to use. Preferably, the ratio of thickening agent to ester is in the range of about 0.5:1 to about 1.5:1.

The PGE compositions of the invention preferably are utilized to provide packaged, multi-part dosage forms in which an actives compartment contains the room temperature stable PGE composition as a unit dose and a diluent compartment contains an aqueous alcohol diluent, which when combined with the PGE composition forms a unit dose for a topical application. In the packaged, multi-part dosage forms embodying the present invention, the actives compartment can also contain a non-aqueous liquid bulking agent, such as a silicone oil (e.g., a polydimethylsiloxane, such as cyclomethicone USP, dimethicone USP, and the like), a $C_6$-$C_{22}$ alcohol (e.g., benzyl alcohol or a fatty alcohol), and the like. The actives compartment, and optionally the diluent compartment, can include a thickening agent, such as a polysaccharide (e.g., a starch, a gum, a starch derivative, or a gum derivative), polyvinylpyrrolidone, polyvinyl alcohol, a cellulose derivative (e.g., hydroxymethyl cellulose, carboxymethyl cellulose, hydroxypropyl methylcellulose, and the like), a sugar (e.g., lactose), and the like.

The multi-component dosage form can comprise a two compartment pouch or packet having a frangible seal between the actives compartment and the diluent compartment, such that squeezing the pouch or packet can breach the seal and allow the contents of the two compartments to combine. The pouch can then be manually kneaded to thoroughly mix and emulsify the contents, affording a cream, ointment, or gel PGE topical dosage form. Alternatively, a clamp or the like can be used in lieu of a frangible seal.

$PGE_1$ and $PGE_2$ are well known to those skilled in the art. Reference may be had to various literature references for its pharmacological activities, side effects and normal dosage ranges. See for example, *Physician's Desk Reference*, 51$^{st}$ Ed. (1997), *The Merck Index*, 12$^{th}$ Ed., Merck & Co., N.J. (1996), and *Martindale The Extra Pharmacopoeia*, 28$^{th}$ Ed., London, The Pharmaceutical Press (1982). Prostaglandin $E_1$ as well as other PGE compounds referenced herein are intended to encompass also the pharmaceutically acceptable derivatives thereof, including physiologically compatible salts and ester derivatives.

The PGE compositions of the invention include a skin penetration enhancer, which is an N,N-di($C_1$-$C_8$)alkylamino substituted, $(C_4$-$C_{18})$alkyl$(C_2$-$C_{18})$carboxylic esters or pharmaceutically acceptable acid addition salts thereof. As used herein, the term "$(C_4$-$C_{18})$alkyl$(C_2$-$C_{18})$carboxylic ester" means an ester of a $(C_4$-$C_{18}$alcohol and a $(C_2$-$C_{18})$carboxylic acid. The term "N,N-di($C_1$-$C_8$)alkylamino substituted," in reference to a $(C_4$-$C_{18})$alkyl$(C_2$-$C_{18})$carboxylic ester means that either the alcohol portion or the carboxylic acid portion from which the ester is prepared bears an amino substituent $NR_xR_y$, wherein $R_x$ and $R_y$ are each independently a $(C_1$-$C_8)$ alkyl group. Preferably $R_x$ and $R_y$ are both methyl groups.

Preferred N,N-di($C_1$-$C_8$)alkylamino substituted, $(C_4$-$C_{18})$ alkyl$(C_2$-$C_{18})$carboxylic esters are dodecyl-2-(N,N-dimethylamino)-propionate (DDAIP); dodecyl-2-(N,N-dimethylamino)-acetate (DDAA); 1-(N,N-dimethylamino)-2-propyl dodecanoate (DAIPD); 1-(N,N-dimethylamino)-2-propyl myristate (DAIPM); 1-(N,N-dimethylamino)-2-propyl oleate (DAIPO); and pharmaceutically acceptable acid addition salts thereof. Particularly preferred is DDAIP, alone or in combination with an auxiliary permeation enhancer. DDAIP is available from Steroids, Ltd. (Chicago, IL). The preparation of DDAIP and crystalline acid addition salts thereof is described in U.S. Pat. No. 6,118,020 to Büyüktimkin, et al., which is incorporated herein by reference. Long chain similar amino substituted, alkyl carboxylic esters can be synthesized from readily available compounds as described in U.S. Pat. No. 4,980,378 to Wong, et al., which is incorporated herein by reference to the extent that it is not inconsistent herewith. Such amino-substituted carboxylic ester penetration enhancers are also sometimes referred to as alkyl-2-(N-substituted amino)-alkanoates and (N-substituted amino)-alkanol alkanoates. For convenient reference, alkyl-2-(N-substituted amino)-alkanoates and (N-substituted amino)-alkanol alkanoates can be grouped together under the term alkyl(N-substituted amino)esters.

The penetration enhancer is present in an amount sufficient to enhance the penetration of the PGE compound into tissue. The specific amount varies necessarily according to the desired release rate and specific form of PGE compound used. Generally, this amount is in the range of about 0.01 percent to about 20 percent, based on the total weight of a topical dosage form to be administered to a patient prepared by mixing a PGE composition of the invention and an aqueous alcoholic diluent, as described herein.

Natural and modified polysaccharides (e.g., gums) can be utilized as a viscosity enhancing agent for the PGE composition. Such thickening agent can optionally be present in the diluent or in both the PGE composition and the diluent. Suitable representative gums are the natural and modified galactomannan gums. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-mannopyranosyl units, linked (1→6) with the main chain, are present as side branches. Galactomannan gums include guar gum, which is the pulverized endosperm of the seed of either of two leguminous plants (*Cyamposis tetragonalobus* and *psoraloids*) and locust bean gum, which is found in the endosperm of the seeds of the carob tree (*Ceratonia siliqua*). Suitable modified polysaccharide gums include ethers of natural or substituted polysaccharide gums, such as carboxylmethyl ethers, ethylene glycol ethers and propylene glycol ethers.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums:Polysaccharides & Their Derivatives*, Whistler R. L. and BeMiller J. N. (eds.), 3$^{rd}$ Ed. Academic Press (1992) and Davidson R. L., *Handbook of Water-Soluble Gums and Resin*, McGraw-Hill, Inc., N.Y. (1980). Most gums are commercially available in various forms, commonly a powder, and ready for use in food and topical compositions. For example, locust bean gum in powdered form is available from Tic Gums Inc. (Belcam, Md.).

Thickening agents preferably are present in the range of about 0.025 to about 40 percent by weight in the PGE compositions of the invention, and about 0.1 percent to about 5 percent by weight, based on the total weight of a topical dosage form prepared by mixing a PGE composition and diluent. The preferred range of thickening agent present in the topical dosage form is about 0.5 percent to 3 percent.

Alternative thickening agents include cross-linked polyacrylic acid polymers and a cellulose derivatives (e.g., carboxymethyl cellulose, hydroxymethyl cellulose, hydroxypropyl methyl cellulose, and the like).

A common variety of polyacrylic acid polymer is known generically as "carbomer." Carbomer is polyacrylic acid polymers lightly cross-linked with polyalkenyl polyether. It is commercially available from the B. F. Goodrich Company (Akron, Ohio) under the designation "CARBOPOL®." A particularly preferred variety of carbomer is that designated as "CARBOPOL®940."

Other polyacrylic acid polymers suitable for use are those commercially available under the designation "PEMULEN™" (B.F. Goodrich Company) and "POLYCARBOPHIL™" (A. H. Robbins, Richmond, Va.). The PEMULEN™ polymers are copolymers of $C_{10}$ to $C_{30}$ alkyl acrylates and one or more monomers of acrylic acid, methacrylic acid or one of their simple esters cross-linked with an allyl ether of sucrose or an allyl ether of pentaerythritol. The POLYCARBOPHIL™ product is polyacrylic acid cross-linked with divinyl glycol.

The concentration of $(C_1-C_4)$-alkyl$(C_8-C_{22})$carboxylic ester (e.g., ethyl laurate, isopropyl myristate, isopropyl laurate, or a mixture of two or more thereof) in the PGE compositions of the invention necessarily varies according to various factors such as the desired semi-solid consistency and the desired skin penetration promoting effects. Suitably, the concentration of $(C_1-C_4)$-alkyl$(C_8-C_{22})$carboxylic ester is the range of about 0.025 percent to about 40 percent by weight based on the total weight of the PGE composition. The preferred composition contains a $(C_1-C_4)$-alkyl$(C_8-C_{22})$carboxylic ester in the range of about 0.5 percent to about 35 percent by weight based on the total weight of the PGE composition.

An optional, but preferred, component is an emulsifier, which can be present in the PGE composition or in the diluent. A suitable emulsifier generally will exhibit a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate, present in an amount up to about 2 percent, based on the total weight of the composition, is preferred. The preferred amount of sucrose stearate emulsifier can also be expressed as a weight ratio of emulsifier to polysacharide gum.

Other suitable emulsifiers are the polyoxyethylene sorbitan esters, long chain alcohols, preferably cetostearyl alcohol, and fatty acid glycerides. Suitable polyoxyethylene sorbitan esters include the monolaurate (TWEEN® 20, SPAN® 20) the monopalmitate (TWEEN® 40), the monostearate (TWEEN® 60), and the monooleate (TWEEN® 80) and mixtures thereof. Preferred fatty acid glycerides include glyceryl monooleate, triolean, trimyristin and tristearin.

Another optional ingredient is an antifoam agent, a chemical that reduces the tendency of the finished preparation to generate foam on shaking or agitation. Silicones are the preferred antifoam agents; however, a wide variety of alcohols and lipids exhibit similar properties. With the exception of alcohols, the selected antifoam agent must be effective in relatively small concentrations, and are employed in trace amounts. Illustrative antifoam agents are dimethicone, cetyl dimethicone, dimethicone silylate, dimethiconol, a mixture of dimethicone and hydrated silica, isopropyl alcohol, hexyl alcohol, trimethylsiloxysilicate, triphenyl trimethicone and the like. A particularly preferred antifoam agent is a mixture of dimethicone with an average chain length of 200 to 300 dimethylsiloxane units and hydrated silica, commercially available under the designation SIMETHICONE® USP from Dow Corning Corporation, Michigan.

The PGE compositions of the invention are substantially free from $C_1-C_4$ alcohols (e.g., methanol, ethanol, and the like). It has been found that lower alkyl alcohols, such as ethanol, can lead to degradation of PGE compounds during storage for prolonged periods of time (e.g., weeks to months). As used herein, the phrase "substantially free from $C_1-C_4$ alcohols" means that the compositions do not contain a destabilizing amount of lower alkyl alcohols. Preferably, the compositions contain not more than trace levels of lower alkyl alcohols, which may be present as a byproduct or contaminant from one or more of the components of the PGE composition (e.g., trace ethanol from ethyl laurate). Typically, the PGE compositions of the invention include not more than about 0.5 percent by weight of $C_1-C_4$ alcohols prior to mixing with a diluent.

Aqueous alcoholic diluents useful for mixing with the PGE compositions of the invention can include one or more buffering agents (i.e., buffer systems), if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents, which are thus responsible for a resistance or change in pH from a starting buffered pH value in the range indicated above are well known. While there are countless suitable buffers, potassium phosphate buffers (e.g., potassium phosphate monohydrate, $KH_2PO_4$ N.F., and the like) have proven effective for compositions of the present invention and are preferred.

The final pH value of the topical composition prepared by the combination of PGE composition and diluent may vary within the physiological compatible range. Necessarily, the final pH value is one not irritating to human skin and preferably such that transdermal transport of the PGE compound is facilitated. Without violating this constraint, the pH may be selected to improve PGE compound stability and to adjust consistency when required. In one embodiment, the preferred pH value is about 3.0 to about 7.4, more preferably about 3.0 to about 6.5, most preferably from about 3.5 to about 6.0.

Preferably, the water present in the diluent is purified, e.g., deionized water. The diluent preferably contains water in the range of more than about 5 to about 95 percent by weight based on the total weight of the diluent. The specific amount of water present is not critical, however, being adjustable to obtain the desired viscosity (usually about 50 cps to about 30,000 cps) and/or concentration of the combination when mixed with the PGE composition. The topical composition formed by mixing the PGE composition and diluent preferably has a viscosity of at least about 30 centipoise. Viscosity enhancing agents can be included to afford the desired level of viscosity. The diluent also preferably includes up to about 95 percent by weight of a $C_1$-$C_4$ alcohol (e.g., ethanol).

PGE compound stabilizers and excipients, such as organic acids and alcohols, cyclodextrins, coloring agents, rheological agents, and preservatives can be added to the extent that they do not limit the stability or penetration of the PGE compound.

The ingredients listed above may be combined in any order and manner that produces a stable composition for ultimately receiving the PGE compound, such as $PGE_1$ and the like, preferably substantially evenly dispersed throughout. Methods of mixing and compounding pharmaceutical compositions, such as the PGE compositions of the invention, are well known in the art.

These compositions can be used for prolonged treatment of peripheral vascular disease, male impotency and other disorders treated or treatable by PGE compounds while avoiding low bioavailability and rapid chemical decomposition associated with other delivery methods.

In one preferred embodiment, the PGE composition comprises about 0.025 percent to about 40 percent by weight of a thickening agent (e.g., guar gum); about 0.025 percent to about 10 percent by weight of a PGE compound, preferably $PGE_1$ (alprostadil), or a pharmaceutically acceptable salt thereof, about 0.025 to about 40 percent by weight of a ($C_1$-$C_4$)-alkyl($C_8$-$C_{22}$)carboxylic ester (e.g., ethyl laurate), and about 0.025 percent to about 40 percent by weight of an N,N-di($C_1$-$C_8$)alkylamino substituted, ($C_4$-$C_{18}$)alkyl($C_2$-$C_{18}$)carboxylic ester skin penetration enhancer (e.g., dodecyl 2-(N,N-dimethylamino)-propionate or a salt thereof).

A preferred diluent for use in a two-part packaged dosage form of the invention comprises 1 to about 20 percent by weight ethanol, 80 to 99 percent by weight water, and a suitable amount of one or more buffering agent to maintain a desired physiologically compatible pH in a topical dosage form prepared by combining the PGE composition and diluent.

Variations in the treating compositions which do not adversely affect the effectiveness of the PGE compound will be evident to one skilled in the art, and are within the scope of this invention. For example, additional ingredients such as coloring agents, anti-microbial preservatives, emulsifiers, lubricants, perfumes, PGE compound stabilizers, and the like, may be included as long as the resulting preparation retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). A fragrance can be included in the composition in an amount up to about 5 percent by weight, based on the total weight of the composition. Suitable perfumes and fragrances are known in the art. A non-limiting example of a suitable fragrance is myrtenol, preferably utilized in an amount of up to about 2 percent by weight.

The compositions of the present invention can also include a small amount (e.g., about 0.01 to about 4 percent by weight) of a topical anesthetic, if desired. Typical topical anesthetics include lidocaine, benzocaine, dyclonine, dibucaine, pharmaceutically acceptable salts and mixtures thereof. In one preferred embodiment, the topical anesthetic is about 0.5 percent dyclonine, based on the weight of the composition.

An illustrative two-component dosage form is set forth below:

|  | Amount, parts by weight | |
|---|---|---|
|  | Preferred | More Preferred |
| Actives compartment | | |
| A PGE compound such as $PGE_1$ | 0.025-10 | 0.5-5 |
| A skin penetration enhancer (e.g., dodecyl 2-(N,N-dimethylamino)-propionate.HCl) | 0.025-40 | 0.5-35 |
| A ($C_1$-$C_4$)-alkyl ($C_8$-$C_{22}$) carboxylic ester (e.g., ethyl laurate) | 0.025-40 | 0.5-35 |
| A viscosity enhancer (e.g., guar gum) | 0.025-40 | 0.5-35 |
| Diluent compartment | | |
| Water (deionized or U.S.P.) | 5-95 | 20-60 |
| Ethanol | 5-95 | 20-60 |
| Phosphate buffer (pH 5.5) | Q.S. | |

If desired, preservatives such as methyl paraben, propyl paraben, benzalkonium chloride, benzethonium chloride, and the like, can be included in the PGE composition and/or the diluent, as well.

The PGE composition and diluent can be combined with agitation to form a topical PGE dosage form.

The present invention is further illustrated by the following examples.

EXAMPLE 1

Alcohol Degrades PGE Compounds

A PGE composition of the invention was prepared by mixing about 3.6 grams of prostaglandin $E_1$, (alprostadil), about 30.1 grams of DDAIP hydrochloride, about 36.1 grams of ethyl laurate, and about 32.6 grams of guar gum. The composition was stored at about 25° C. for a month.

The stability of the PGE composition was assessed by high performance liquid chromatography (HPLC). The absence of significant amounts of $PGA_1$ and $PGB_1$ in the compositions was taken as an indicator of stability ($PGA_1$ and $PGB_1$ are byproducts of $PGE_1$ degradation). For comparison, a solution of prostaglandin $E_1$ (4 mg) in ethanol (1 mL) was prepared and stored at the same temperature and for the same time period as the PGE composition. After a month of storage, the PGE composition contained only about 0.2 percent $PGA_1$ (based on HPLC peak areas). In contrast, the ethanol solution of $PGE_1$ contained about 1 percent $PGA_1$ after one month of storage, indicating degradation of the $PGE_1$ occurred in the presence of ethanol.

EXAMPLE 2

Fatty Esters Stabilize PGE Compounds

A topical PGE composition was prepared by mixing about 0.4 parts by weight $PGE_1$, about 0.5 parts by weight DDAIP hydrochloride, about 3 parts by weight ethyl laurate, about 2.5 parts by weight guar gum, about 5 parts by weight ethanol, and about 88.6 parts by weight aqueous phosphate buffer (pH 5.5). For comparison, a similar composition was prepared having the same amount of each component, but omitting the ethyl laurate, and having a correspondingly larger amount of buffer.

The storage stability (15° C.) of each composition was evaluated over 8 weeks by HPLC as described above, but also monitoring for DDAIP and the degradation byproduct 8-iso$PGE_1$, in addition to $PGA_1$ and $PGB_1$. The results are shown in Table 1.

TABLE 1

| Time | HPLC Stability With Ethyl Laurate (% based on peak area) | | | | | HPLC Stability Without Ethyl Laurate (% based on peak area) | | | | |
|---|---|---|---|---|---|---|---|---|---|---|
| | $PGE_1$ | $PGA_1$ | $PGB_1$ | i-$PGE_1$ | DDAIP | $PGE_1$ | $PGA_1$ | $PGB_1$ | i-$PGE_1$ | DDAIP |
| initial | 94.40 | 0.40 | ND* | ND | 103.80 | 95.95 | 1.05 | ND | 0.95 | 90.68 |
| 1 wk | 96.70 | 0.70 | ND | ND | 98.88 | 90.10 | 4.00 | 1.75 | 2.40 | 77.44 |
| 2 wk | 96.85 | 0.95 | ND | ND | 98.32 | 88.35 | 6.35 | 5.50 | 2.15 | 67.28 |
| 3 wk | 97.40 | 1.10 | ND | ND | 96.36 | 72.35 | 6.55 | 6.75 | 1.75 | 70.44 |
| 4 wk | 94.75 | 1.10 | ND | ND | 93.28 | 77.45 | 8.80 | 11.55 | ND | 48.44 |
| 5 wk | 99.90 | 1.70 | ND | 0.25 | 96.56 | 83.15 | 10.60 | 15.00 | 0.90 | 43.84 |
| 8 wk | 94.00 | 2.65 | ND | ND | 100.76 | 81.00 | 14.90 | 17.35 | ND | 37.92 |

*ND = not detected

The data in Table 1 clearly show that ethyl laurate has a stabilizing effect on $PGE_1$ and DDAIP, even in the presence of ethanol.

The foregoing examples have been provided as an illustration of preferred embodiments of the invention, and are not meant to limit the scope of the invention.

We claim:

1. A storage stable prostaglandin E group composition comprising:
   (a) a prostaglandin E group compound;
   (b) a $(C_1-C_4)$-alkyl$(C_8-C_{22})$carboxylic ester;
   (c) an N,N-di$(C_1-C_8)$alkylamino substituted, $(C_4-C_{18})$alkyl$(C_2-C_{18})$carboxylic ester, a pharmaceutically acceptable addition salt thereof, or a combination thereof; and
   (d) optionally, a viscosity enhancing agent;
   the composition being substantially free from $C_1-C_4$ alcohols.

2. The composition of claim 1 wherein the prostaglandin E group compound is selected from the group consisting of prostaglandin $E_1$, prostaglandin $E_2$, and prostaglandin $E_3$.

3. The composition of claim 1 wherein the $(C_1-C_4)$-alkyl $(C_8-C_{22})$carboxylic ester comprises ethyl laurate.

4. The composition of claim 1 wherein the N,N-di$(C_1-C_8)$ alkylamino substituted, $(C_4-C_{18})$alkyl$(C_2-C_{18})$carboxylic ester comprises dodecyl 2-(N,N-dimethylamino)-propionate or a pharmaceutically acceptable addition salt thereof.

5. The composition of claim 1 including a viscosity enhancing agent selected from the group consisting of a polysaccharide and a modified polysaccharide.

6. The composition of claim 1 comprising guar gum as the viscosity enhancing agent.

7. A storage stable prostaglandin group composition comprising:
   (a) about 0.025 percent to about 10 percent by weight of a prostaglandin E group compound;
   (b) about 0.025 to about 40 percent by weight of a $(C_1-C_4)$-alkyl$(C_8-C_{22})$carboxylic ester;
   (c) about 0.025 to about 40 percent by weight of an N,N-di$(C_1-C_8)$alkylamino substituted, $(C_4-C_{18})$alkyl$(C_2-C_{18})$carboxylic ester, a pharmaceutically acceptable addition salt thereof, or a combination thereof; and
   (d) about 0.025 to about 40 percent by weight of a viscosity enhancing agent;
   the composition being substantially free from $C_1-C_4$ alcohols.

8. The composition of claim 7 wherein the prostaglandin E group compound is selected from the group consisting of prostaglandin $E_1$, prostaglandin $E_2$, and prostaglandin $E_3$.

9. The composition of claim 7 wherein the $(C_1-C_4)$-alkyl $(C_8-C_{22})$carboxylic ester comprises ethyl laurate.

10. The composition of claim 7 wherein the N,N-di$(C_1-C_8)$ alkylamino substituted, $(C_4-C_{18})$alkyl$(C_2-C_{18})$carboxylic ester comprises dodecyl 2-(N,N-dimethylamino)-propionate or a pharmaceutically acceptable addition salt thereof.

11. The composition of claim 7 wherein the viscosity enhancing agent is selected from the group consisting of a polysaccharide and a modified polysaccharide.

12. The composition of claim 7 wherein the viscosity enhancing agent comprises guar gum.

13. The composition of claim 7 wherein the prostaglandin E group compound comprises about 0.5 to about 5 percent by weight prostaglandin $E_1$.

14. The composition of claim 7 wherein the $(C_1-C_4)$-alkyl $(C_8-C_{22})$carboxylic ester comprises about 0.5 to about 35 percent by weight ethyl laurate.

15. The composition of claim 7 wherein the N,N-di$(C_1-C_8)$ alkylamino substituted, $(C_4-C_{18})$alkyl$(C_2-C_{18})$carboxylic ester comprises about 0.5 to about 35 percent by weight dodecyl 2-(N,N-dimethylamino)-propionate or a pharmaceutically acceptable addition salt thereof.

16. The composition of claim 7 wherein the viscosity enhancing agent comprises about 0.5 to about 35 percent by weight guar gum.

17. A storage stable prostaglandin E group composition comprising:
   (a) about 0.025 percent to about 10 percent by weight of prostaglandin $E_1$;
   (b) about 0.025 to about 40 percent by weight of a ethyl laurate;

(c) about 0.025 to about 40 percent by weight of dodecyl 2-(N,N-dimethylamino)-propionate or a pharmaceutically acceptable addition salt thereof; and
(d) about 0.025 to about 40 percent by weight of guar gum; the composition being substantially free from $C_1$-$C_4$ alcohols.

18. A multi-part dosage form suitable for preparing a topical prostaglandin E composition comprising;
(a) a sealed actives compartment comprising a composition of claim 1; and
(b) a sealed diluent compartment comprising an aqueous diluent including a $C_1$-$C_4$ alcohol, water, and optionally a pH buffering agent.

19. The multi-pan dosage form of claim 18 wherein the $C_1$-$C_4$ alcohol in the diluent is ethanol.

20. A multi-pan dosage form suitable for preparing a topical prostaglandin E composition comprising;
(a) a sealed actives compartment comprising a composition of claim 7; and
(b) a sealed diluent compartment comprising an aqueous diluent including a $C_1$-$C_4$ alcohol, water, and optionally a pH buffering agent.

21. The multi-pan dosage form of claim 20 wherein the $C_1$-$C_4$ alcohol in the diluent is ethanol.

22. A multi-part dosage form suitable for preparing a topical prostaglandin E composition comprising;
(a) a sealed actives compartment comprising a composition of claim 17; and
(b) a sealed diluent compartment comprising an aqueous diluent including a $C_1$-$C_4$ alcohol, water, and optionally a pH buffering agent.

23. The multi-part dosage form of claim 22 wherein the $C_1$-$C_4$ alcohol in the diluent is ethanol.

24. The composition of claim 1 including a viscosity enhancing agent which is a cellulose derivative selected from the group consisting of carboxymethyl cellulose, hydroxymethyl cellulose and hydroxypropylmethyl cellulose.

25. The composition of claim 1 including cross-linked polyacrylic acid as the viscosity enhancing agent.

26. The composition of claim 7 wherein the viscosity enhancing agent is a cellulose derivative selected from the group consisting of carboxymethyl cellulose, hydroxymethyl cellulose, and hydroxypropylmethyl cellulose.

27. The composition of claim 7 wherein the viscosity enhancing agent is cross-linked polyacrylic acid.

* * * * *

UNITED STATES PATENT AND TRADEMARK OFFICE
CERTIFICATE OF CORRECTION

PATENT NO. : 7,560,489 B2 Page 1 of 1
APPLICATION NO. : 11/546196
DATED : July 14, 2009
INVENTOR(S) : Daniel W. Frank et al.

It is certified that error appears in the above-identified patent and that said Letters Patent is hereby corrected as shown below:

Column 1,
Line 16, "intracavemously" should be -- intracavernously --.

Column 10,
Line 3, after "prostaglandin" insert -- E --.

Column 11,
Lines 14, 16 and 23, "multi-pan" should be -- multi-part --.

Signed and Sealed this

First Day of December, 2009

David J. Kappos
*Director of the United States Patent and Trademark Office*